(12) United States Patent
Sagel et al.

(10) Patent No.: US 9,717,665 B2
(45) Date of Patent: Aug. 1, 2017

(54) TOOTH DESENSITIZING ORAL CARE COMPOSITIONS, DEVICES, AND METHODS

(71) Applicant: The Procter & Gamble Company, Cincinnati, OH (US)

(72) Inventors: Paul Albert Sagel, Maineville, OH (US); Lan Ngoc Nguyen, Marion, IN (US); Adam Michael Tunis, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 117 days.

(21) Appl. No.: 14/525,290

(22) Filed: Oct. 28, 2014

(65) Prior Publication Data
US 2015/0118166 A1  Apr. 30, 2015

Related U.S. Application Data
(60) Provisional application No. 61/896,361, filed on Oct. 28, 2013.

(51) Int. Cl.
*A61K 8/362* (2006.01)
*A61K 8/02* (2006.01)
*A61Q 11/00* (2006.01)

(52) U.S. Cl.
CPC ............ *A61K 8/362* (2013.01); *A61K 8/0216* (2013.01); *A61Q 11/00* (2013.01); *A61K 2800/74* (2013.01)

(58) Field of Classification Search
USPC .......................................................... 424/53
See application file for complete search history.

(56) References Cited

U.S. PATENT DOCUMENTS

| | | | |
|---|---|---|---|
| 5,211,559 A | 5/1993 | Hart et al. | |
| 5,597,552 A | 1/1997 | Herms et al. | |
| 5,855,870 A | 1/1999 | Fischer | |
| 5,980,249 A | 11/1999 | Fontenot | |
| 6,361,319 B2 | 3/2002 | Cox | |
| 6,423,301 B1 | 7/2002 | Cox | |
| 6,500,407 B1 | 12/2002 | Cox | |
| 6,506,055 B1 | 1/2003 | Pashley et al. | |
| 6,582,680 B2 | 6/2003 | Cox | |
| 8,632,754 B2 | 1/2014 | Sharma | |
| 2002/0041852 A1 | 4/2002 | Napolitano et al. | |
| 2003/0215401 A1 | 11/2003 | Estrada et al. | |
| 2004/0005277 A1 | 1/2004 | Wilson et al. | |
| 2007/0231277 A1* | 10/2007 | Sharma .................. | A61K 8/22 424/53 |
| 2010/0322984 A1 | 12/2010 | Rees et al. | |
| 2010/0322988 A1 | 12/2010 | Prencipe et al. | |
| 2012/0027828 A1 | 2/2012 | Kleinberg et al. | |
| 2012/0322024 A1 | 12/2012 | De Vreese et al. | |
| 2013/0272970 A1 | 10/2013 | Pimenta et al. | |
| 2014/0060156 A1 | 3/2014 | Heipp et al. | |
| 2014/0060157 A1 | 3/2014 | Sharma et al. | |
| 2014/0060158 A1 | 3/2014 | Heipp et al. | |
| 2014/0060159 A1 | 3/2014 | Sharma et al. | |

FOREIGN PATENT DOCUMENTS

| | | |
|---|---|---|
| JP | 2005-187331 A | 7/2005 |
| WO | WO 2009/106972 A2 | 9/2009 |

OTHER PUBLICATIONS

PCT International Search Report dated Feb. 5, 2015—4 pages.
Ishihata, Hiroshi et al., "In Vitro Dentin Permeability After Application of Gluma Desensitizer as Aqueous Solution or Aqueous Fumed Silica Dispersion", Journal Applied Oral Science, 2011:19(2), pp. 147-153.
PCT International Search Report and Written Opinion for PCT/US2014/062564 dated Feb. 5, 2015.

\* cited by examiner

*Primary Examiner* — Walter Webb
(74) *Attorney, Agent, or Firm* — Kelly L. McDow

(57) ABSTRACT

Desensitizing oral care composition useful for treating dentinal hypersensitivity, comprising potassium oxalate and methods of use thereof. Delivery systems including a strip of material and such oral care compositions for the treatment of dentinal hypersensitivity and methods of use thereof.

20 Claims, 5 Drawing Sheets

TOOTH DESENSITIZING ORAL CARE COMPOSITIONS, DEVICES, AND METHODS

CROSS REFERENCE TO RELATED APPLICATIONS

This application claims the benefit of U.S. Provisional Application Ser. No. 61/896,361, filed Oct. 28, 2013, the entirety of which is incorporated by reference herein.

FIELD OF THE INVENTION

The present invention relates to tooth desensitizing oral care compositions, strip-type delivery devices and methods of use wherein the compositions contain a dentinal tubule blocker.

BACKGROUND OF THE INVENTION

Tooth sensitivity, including dentinal hypersensitivity, has become identified as a common problem among consumers. Dentinal hypersensitivity is a condition where dentin is exposed due the lack of soft tissues covering the surfaces. The exposed dentin includes small tubules which are susceptible to triggering of a pain response from a variety of stimuli such as heat, cold, sour taste, or pressure. The level of pain can range from an ache or soreness to a shooting pain. The most common approach for over-the-counter, at-home treatment of dentinal hypersensitivity is the use of dentifrices containing desensitizing agents such as SENSODYNE PRONAMEL (contains 5% potassium nitrate) and NOVAMIN (contains bioactive glass). While such products can provide some relief, reduction of sensitivity through dentifrice use alone is limited for several reasons including: inherent limitations on the contact time of the dentifrice to the exposed dentin (as brushing time may be relatively short); dilution of the desensitizing agent by saliva; typical usage includes rinsing one's mouth out after brushing reducing the amount of desensitizing agent delivered to the tooth; and inherent limitations on the amount of desensitizing agent that may be stably formulated into a dentifrice formulation. A need therefore exists for an improved treatment for dental hypersensitivity that can be easily performed at home.

Oxalate salts can act as dentinal tubule blockers that can thereby be useful for the treatment of dental hypersensitivity. Potassium oxalate is a preferred desensitizing agent as it forms calcium oxalate upon delivery to the open tubules. Formation of the calcium oxalate blocks the dentinal tubules and may prevent environmental stimuli from causing sensitivity pain.

A product called SUPERSEAL is a commercially available dental sensitivity treatment product available from Phoenix Dental. The SUPERSEAL product is in liquid form and is sold in a small bottle. The bottle contains a 2.9% solution of a potassium oxalate salt, $K_3H(C_2O_4)\cdot 2H_2O$ at a pH of 1.5 (approximately 1.0% of oxalate ion). The instructions for use include painting or swabbing the liquid in the oral cavity. Although the product does help with dental hypersensitivity, it can be difficult for consumers to know how much to apply and/or to target a single area for treatment, and contact time of the potassium oxalate at the sensitivity site may be transient due to dilution with saliva.

Similarly, a LISTERINE brand rinse is commercially available in the United Kingdom that contains dipotassium oxalate and has a pH of 4.3. Again, the presence of the potassium oxalate in the mouth is transient and here, it is considerably difficult to target a particular area of sensitivity with a rinse product.

The combination of adhesive-building polymer with potassium oxalate has been attempted in another commercial tooth desensitizing product, SENZZZZZAWAY, available from Majestic Drug (New York, USA). SENZZZZZAWAY is a single-use blister packed product containing a composition that includes a CARBOPOL (CARBOPOL is the trade name for a general class of high molecular weight homo and co-polymers of acrylic acid crosslinked with a polyalkenyl polyether, commercially available from Lubrizol Advanced Materials, Inc. (Ohio, USA), thickener and 2.5% (as added) of an oxalate salt ($KHC_2O_4+HNO_3$) at a pH of 0.7. The product is packaged with a small brush and the instructions include brushing the product onto the area to be treated. If potassium oxalate is applied to the wrong part of the oral cavity and/or for too short of a period of time, it is possible that no benefit is garnered or that the crystal deposition occurs at the wrong site. A need therefore still exists for a sensitivity product that can reach the desired location, deliver the desired chemistry, and for the desired amount of time. The prior literature discloses that potassium oxalate works but also has disclosed it as being ineffective for dentinal tubule blocking. Without being limited by theory, it is now believed that some of the ineffectiveness was wrongly associated with the potassium oxalate mechanism itself when it was likely just the wrong selection of contact time, delivery device, pH, and the like.

Strip-form oral care delivery systems are commercially available, such as tooth-whitening strips including those sold under the name CREST WHITESTRIPS by the Procter & Gamble Company (Cincinnati, Ohio, USA). The popularity of the strip format has expanded to include strips for fluoride treatment and sensitivity treatment (for example, SHEER FLUORX and SHEER DESENZ strip tooth treatment products, both commercially available from the CAO Group, Utah, USA).

Further, the literature discussing delivery systems for tooth-whitening also often generally disclose that the same delivery systems may be used with sensitivity agents. However, due to the fundamental differences between whitening agents and potassium oxalate, it has been surprisingly found that the compositions previously found to be useful in conjunction with whitening strip products are unsuitable for the delivery of potassium oxalate.

A tooth sensitivity delivery kit including a preformed tray and a bulky foam strip (approximately 6 cm long, 1 cm tall, 1 cm thick) impregnated with a potassium oxalate solution that sits inside the tray is commercially available under the trade name REMESENSE from Sylphar (Belgium). Although providing some efficacy, the REMESENSE tray system is bulky and uncomfortable for consumers during use. Further, due to the porosity of the impregnated foam, the potassium oxalate solution settles (due to gravity) into the lowest portion of the foam, making application to the gum line difficult (if not impossible) and the delivery system only suited for use with the upper arch, not the lower arch. Further, it is difficult to provide targeted relief to an area in need of treatment through the use of the REMESENSE tray and foam.

The need therefore exists for a dentinal hypersensitivity treatment product that can provide directed, sustained delivery of a desensitizing agent to a desirable area in the oral cavity, for a period of time sufficient to provide significant tubule blockage and subsequent sensitivity relief.

SUMMARY OF THE INVENTION

Without being limited by theory, it has surprisingly been found that strip-type delivery systems can provide directed, sustained delivery of a desensitizing agent to a desired area in the oral cavity, for a period of time sufficient to provide significant tubule blockage and subsequent sensitivity relief.

In some aspects, the present invention relates to desensitizing oral care compositions useful for treating dentinal hypersensitivity, including a) at least 40%, by weight of the composition, of water; b) from about 0.01% to about 25%, by weight of the composition, of a desensitizing agent selected from oxalic acid, salts of oxalic acid, and mixtures thereof; c) from about 0.1% to about 30%, by weight of the composition, of an adhesive polymer thickener; d) from about 0.5% to about 40%, by weight of the composition, of a secondary structuring polymer thickener; e) optionally from about 10% to about 40%, by weight of the composition, of a humectant; f) less than 0.1%, by weight of the composition, of abrasive; wherein the composition has a pH of less than 10.

The present invention further relates to such compositions wherein the composition exhibits a delta angle value of less than about 35°; and/or wherein the complex modulus is according to Equation 1.

The present invention further relates to delivery systems for such desensitizing oral care compositions comprising: a) a strip of material; a desensitizing oral care composition; and optionally a release liner.

The present invention further relates to such delivery systems wherein the desensitizing oral care composition comprises: from about 50% to about 65%, by weight of the composition, of water; from about 1% to about 5%, by weight of the composition, of a desensitizing agent selected from oxalic acid, potassium salts of oxalic acid, and mixtures thereof; from about 0.5% to about 10%, by weight of the composition, of an adhesive polymer thickener; from about 1% to about 20%, by weight of the composition, of a secondary structuring polymer thickener; from about 25% to about 40%, by weight of the composition, of a humectant; and less than 0.1%, by weight of the composition, of abrasive; and a release liner comprised of polypropylene film.

The present invention further relates to such compositions and delivery systems wherein the humectant comprises glycerin.

The present invention further relates to such compositions and delivery systems wherein the composition comprises a Delta angle less than 30° and greater than 15°.

The present invention further relates to such compositions and delivery systems wherein the composition comprises the secondary structuring polymer in an amount equal to or greater than the amount of adhesive-building polymer.

The present invention further relates to such compositions and delivery systems wherein the ratio of the adhesive polymer to the secondary structuring polymer is from about 1:1 to about 1:5.

The present invention further relates to such compositions and delivery systems wherein the composition comprises from about 1% to about 6% of the desensitizing agent.

The present invention further relates to such compositions and delivery systems wherein the desensitizing agent is selected from potassium oxalate salts and mixtures thereof.

The present invention further relates to such compositions and delivery systems wherein the adhesive-building polymer is selected from high molecular weight homo and co-polymers of acrylic acid crosslinked with a polyalkenyl polyether, and mixtures thereof.

The present invention further relates to such compositions and delivery systems wherein the secondary structuring polymer is selected from carboxymethylcelluloses and mixtures thereof.

DETAILED DESCRIPTION OF THE INVENTION

Figure 1:
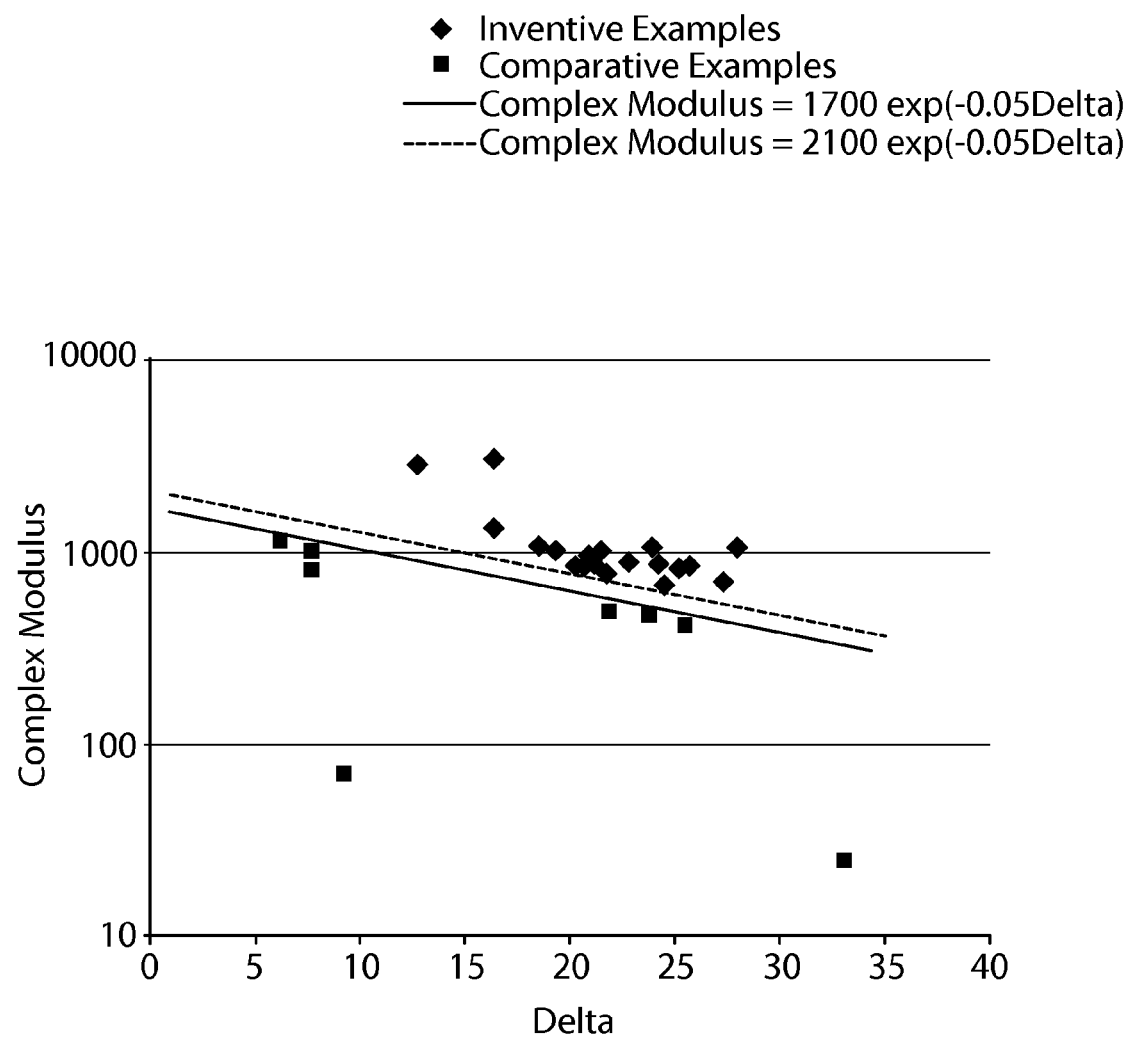
FIG. 1 is a graphical representation of Example I plotting the Complex Modulus versus the Delta values for the compositions shown in Tables 1A, 1B, 1C, 1D, 2A and 2B. The solid black line represents Equation 1 and the dashed black line represents Equation 2.

In some aspects, the strip-type delivery systems disclosed include a strip of material, a desensitizing oral care composition, and optionally include a release liner. The desensitizing oral care compositions may include a desensitizing agent, an adhesive-building polymer, a secondary structuring polymer, and water. Methods of using such delivery systems are also described. These delivery systems and methods, as well as other optional components are discussed more fully, below. Again without being limited by theory, oxalates may be a preferred anti-sensitivity agent as they form calcium oxalate upon delivery to the open tubules. Formation of the calcium oxalate blocks the dentinal tubules to prevent environmental stimulus from causing sensitivity pain. The overall design of the strip-type delivery system which applies oxalate is important to product performance, stability, application and manufacturability.

Delivery System

Delivery systems useful for applying a desensitizing agent to the oral cavity may include a strip of material, a desensitizing oral care composition, and, optionally, a release liner.

The strip of material may have at least two sides. The desensitizing oral care composition may be applied to at least one side of the strip of material, and, optionally, a release liner is applied to protect the composition during storage and/or transportation.

Without being limited by theory, it is believed that in order to effectively deliver the desensitizing agents, it is important to select an appropriate strip of material, appropriate oral care compositional elements, and appropriate rheological characteristics of the composition to ensure that the delivery system is a) stable during storage and shipment;

b) that the desensitizing agent releases from the composition to the targeted area; c) that the delivery device adheres to the desired location in the oral cavity for the desired period of time; and/or d) when a release liner is used, that the strip and composition can sufficiently release from the liner without leaving more than half of the composition behind.

Strip of Material

The delivery system may include a strip of material. As used herein, "strip of material" generally refers to section of thin material having a length longer than the width, and a thickness less than the width. An example is a length from about 2 to about 3 times the width. Alternatively, the length may be from about 1 cm to about 10 cm, and the width may be from about 0.1 cm to about 10 cm. Alternatively the width may be from about 0.25 to about 5 cm, alternatively from about 0.25 to about 2 cm, alternatively from about 0.75 to about 2 cm, alternatively about 1 cm. In an example, the length is from about 1 to about 5 cm, alternatively from about 2 to about 5 cm.

While the thickness of the film may vary, the film may have a thickness between about 0.1 micrometer and about 1500 micrometers (μm).

The strip of material may serve as a protective barrier for the desensitizing oral care composition. It may prevent substantial leaching and/or erosion of the desensitizing oral care composition for a selected period of time, or altogether. Such leaching and/or erosion could be caused, for example, by contact between the composition and the wearer's lips, tongue, or saliva. Preventing substantial leaching or erosion allows the active in the desensitizing oral care composition to act upon the oral surface for an extended period of time, from several seconds to several hours. The term "act upon" is herein defined as bringing about the deposition of oxalate and oxalate-containing precipitates or crystals on the surface to be treated (including dentin, enamel, pellicle, and smear layers, or combinations thereof). "Act upon" can include formation of oxalate crystals in the dentinal tubules.

Although strip-type delivery systems have now become common for tooth-whitening, it should be understood that the usage of such delivery systems for delivering desensitizing agents is different in several regards. The selection of the appropriate strip materials is surprisingly different. It is contemplated that some strips of material will be preferred over others for reasons of application and wearability depending on the desensitizing oral care composition used.

Unlike in whitening strips, where the whitening target surface is predominantly the teeth, treating dentinal hypersensitivity typically involves treating oral surfaces at or near the gumline, where the exposed tubules typically reside. To ensure good coverage of the gumline, the strip can therefore be sized to cover a portion of the soft gingival tissue and a portion of the harder tooth tissues (enamel and, if present, exposed dentin). It may not be critical to cover all of the harder tooth tissues to effectively reduce sensitivity. The region of application can be anywhere on the upper or lower dental arch and is typically (although not always) on the buccal surfaces (cheek side). Because some of the regions of sensitive teeth are in the posterior regions (back teeth) it becomes much easier to apply the strip if one hand can be used to hold and apply the strip while the other hand is used to pull back the lip and cheek areas and apply the strip directly. Holding the strip with one hand and applying it requires the strip to have sufficient stiffness to handle and hold it, yet still posses enough flexibility to conform to the shape of the tissues and teeth the strip is being applied to. As a result, there is an optimum range of strip physical properties which result in good handling and conformability to the sensitivity surfaces being treated, and these properties do not necessarily correlate to the properties desirable for delivering other kinds of oral care compositions. The preferred flexural stiffness and size/shape of the strip used in the disclosed delivery systems are in some aspects different than those typically used for whitening strip products.

The delivery system may be sized to cover a large portion, or even the entire maxillary or mandibular gumline. Many people experience sensitivity in fewer than all of their teeth. Therefore, it may be useful to provide a delivery system sized to cover less than most of the maxillary or mandibular gumline, such as about half of the maxillary or mandibular gumline, or even less than half of the maxillary or mandibular gumline.

The delivery system may include a strip of material comprising a textured film. The film may be textured on one side and flat, or untextured, on the other side. The desensitizing oral care composition may be applied to the flat side.

The delivery system may include a strip of material that is conducive to being cut by a rotary die on a release liner, through a process called "kiss cutting." In a kiss cutting process, it may be desirable to cut the film without cutting completely through the release liner during processing.

The strip of material may be a solid layer, or may have pores, channels, or other openings that run from one side of the strip to an opposite, facing side of the strip. The strip of material may be water-permeable or water-impermeable. For example, if the composition requires hydration for improved efficacy or distribution, a water-permeable material may be desirable. A strip of material is water-permeable if water can pass through the material at a rate of at least 0.5 g/cm2/hour.

Material

Materials useful for the strip of material include a wide variety of materials, and can be in a single layer, or multiple layers, or can be in an irregular pattern of layers. As examples, the material may be a mesh or otherwise have gaps or holes in the layer. The material may be formed with gaps or holes, or may be punctured or otherwise processed or treated to create gaps or holes in the layer.

The strip of material can be dissolvable. In multi-layer materials, one or more portions or layers of the strip may be dissolvable. In multi-layer materials, one or more portions or layers of the strip may be dissolvable, and other portions or layers of the strip may be indissolvable. If more than one dissolvable portion or layer is present, some portions or layers may dissolve at a different rate than other portions or layers. Exemplary dissolvable materials are described, for example, in U.S. Patent Application Publication 2005/0208110.

Figure 2:
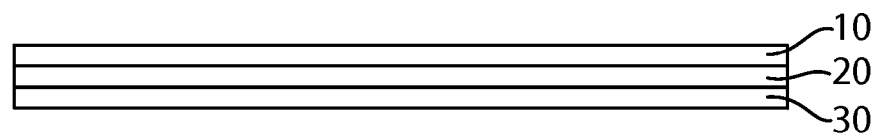
FIG. 2 is a schematic side view of an exemplary, multi-layer strip.

The strip may be multi-layered and dissolvable at least in part to deliver agents sequentially to the oral cavity. As a non-limiting example, a potassium oxalate-containing inner layer may be combined with a calcium chloride-containing middle- or outer layer. FIG. 2 shows a schematic side view of a multi-layer strip having an inner layer 10, a middle-layer 20, and an outer layer 30. It should be understood that in a physical strip, distinct layers may be difficult or impossible to visualize with the naked eye, particularly if one or more of the layers is very thin, or if the layers have similar visual appearance. As used herein, an "inner" refers to a position nearer the teeth and/or gums when the strip is applied in the mouth as intended, and "outer" refers to a position nearer the cheek or further from the teeth and gums when the strip is applied in the mouth as intended. An inner layer need not be (but could be) the innermost layer of the strip of material, just as an outer layer need not be (but could be) the outermost layer of the strip of material. As used herein, the relative positions of inner and outer layers are described at the time of application, before any layers have dissolved (if dissolvable layers are used), unless expressly stated otherwise.

Upon application to the teeth and gums, the potassium oxalate-containing inner layer may dissolve first, releasing oxalate into the tubule fluid of open tubules. In some embodiments, the dissolution of the potassium oxalate-containing inner layer may not be required to deliver the oxalate to the tubule fluid. For example, oxalate may diffuse from the inner layer, and the dissolution of the inner layer may expose another layer or layers. The calcium chloride-containing middle- or outer layer may dissolve after the potassium oxalate-containing inner layer, releasing calcium near the tubule. The release of calcium near the tubules recently treated with oxalate can further the formation of occlusive calcium oxalate crystals in or near the tubules, which in turn may decrease sensitivity associated with open tubules. As with the inner layer, it may not be essential for the calcium chloride-containing outer layer to dissolve at all, or it may not be essential for the calcium chloride-containing outer layer to dissolve in order to deliver calcium in or near the tubules.

By modifying the strip of material composition, size, and layers, the delivery of the desensitizing agent may be modified.

The strip of material may comprise polymers, natural and synthetic woven materials, non-woven materials, foil, paper, rubber, or combinations thereof. The material may be selected from films and may include one or more polymers. Non-limiting, exemplary polymers useful in the strip of materials include polyolefins (e.g. polyethylene), ethylvinylacetate, polyesters, ethylvinyl alcohol, and combinations thereof. Examples of polyesters include Mylar® and fluoroplastics such as Teflon®, both manufactured by DuPont. In some embodiments, the strip of material may comprise polyethylene. The strip of material may comprise a blend of high density and low density polyethylene. An exemplary blend of high density and low density polyethylene is a combination of about 90% HDPE with about 10% LDPE.

The strip of material may be formed by a cast or blown process. In some preferred embodiments, the strip of material is cast. Casting may provide better control over the caliper of a film of certain thicknesses. The strip of material may be embossed with a pattern or texture, such as an array of pyramid shapes. Such textures may provide tactile feedback to a user, and may make it easier to place or confirm the placement of the strip, especially, but not exclusively, if the strip is translucent, transparent, or otherwise difficult to see against the teeth. The strip of material may have about 25-35 grams of polymer per square meter of film. The strip of material is generally less than or equal to about 1 mm thick, preferably less than about 0.05 mm thick, and more preferably from about 0.001 to about 0.03 mm thick. A polyethylene strip of material is preferably less than about 0.1 mm thick and more preferably from about 0.005 to about 0.02 mm thick.

Figure 3:
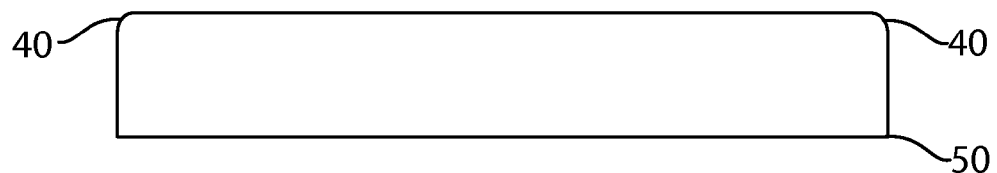
FIG. 3 is the silhouette of an exemplary strip of material.

The shape of the strip of material is any shape and size that covers the desired oral surface. Preferably the strip of material has rounded corners. As illustrated in an exemplary embodiment in FIG. 3, rounded corners 40 are defined as not having any sharp angles or points 50. Rounded corners may help avoid gum irritation that may occur with sharp edges. In some embodiments, all corners of the strip of material are rounded. In some embodiments, corners of the strip of material intended to contact the gums or other soft tissues are rounded.

The strip of material may contain shallow pockets. When the desensitizing oral care composition is coated on a strip of material, additional oral care composition fills shallow pockets to provide reservoirs of additional oral care composition. Additionally, the shallow pockets may help to provide texture to the delivery system. The film may have an array of shallow pockets. Generally, the shallow pockets, if used, are approximately 0.4 mm across and 0.1 mm deep. The shallow pockets may be formed within a particular layer of the strip of material, or may be formed by layering two or more materials, e.g., by layering a mesh over another layer.

When shallow pockets are included in the strip of material and oral care compositions are applied to it in various thicknesses, the overall thickness of the delivery system is generally less than about 1 mm Preferably, the overall thickness is less than about 0.5 mm.

Usage and Making

The strip of material may be held in place on the oral surface by adhesive attachment provided by the desensitizing oral care composition. The viscosity and general tackiness of the desensitizing oral care composition cause the strip of material to be adhesively attached to the oral surface without substantial slippage from the frictional forces created by the lips, teeth, tongue and other oral surfaces rubbing against the strip of material while talking, drinking, etc. However, the adhesion to the oral surface should be low enough to allow the strip of material to be easily removed by the wearer by simply peeling off the strip of material using one's finger or fingernail, or by rubbing the strip of material with a soft implement, such as cotton balls, swabs or gauze pads.

Strips may be used at least twice, or at least three times, or at least up to five times, for best effect. A new or fresh strip may be used for each treatment. Repeated deposition of oxalate, for example, has been shown to significantly reduce flow rates through dentin, as measured by Example 3, below, which should correlate to significantly reduced sensitivity in vivo.

The strip of material may be formed by several of the film making processes known in the art. In some embodiments, a strip of material made of polyethylene is made by a blown process or a cast process. Other processes, including extrusion, are also feasible. Additionally, the desensitizing oral care composition may be incorporated onto the strip during the processing of the strip. The desensitizing oral care composition may be a laminate on the strip.

Size and Shape of the Strip of Material

Strips having a shorter length can be less rigid than longer strips due to the handling during application. Rigidity can be measured as flexural stiffness, using a Handle-O-Meter instrument, available from Thwing-Albert Instrument Co. of Philadelphia, Pa. (such as model #211-300, or equivalent), according to ASTM test method D2923-95. The strip of material may have a flexural stiffness less than about 50 grams/centimeter. Strips in the range of 1-5 cm in length are preferred for application to the posterior dentition, if application to the posterior dentition is desired. Shorter strips may be most useful where sensitivity is localized to a tooth or a small number of teeth. Longer strips may be most useful where sensitivity occurs at multiple teeth, or where the user is uncertain precisely where (e.g., which tooth or part of a tooth) the sensitivity originates. This is different from strips for whitening or other cosmetic purposes, which may be applied only to the most visible teeth at the front of the mouth. For cosmetic purposes, the range of coverage desired is typically much smaller than it might be for sensitivity reduction. Further, the handling properties of a sensitivity strip do not necessarily match those of a strip for cosmetic purposes, since a sensitivity strip may be applied to the back teeth, where soft tissues may interfere with application of the strip.

The width of the strip may also contribute to ease of handling and applying the strip. Without being limited by theory, if the strip is too wide, less stiff strip materials may tend to curl over on themselves while being handled. This may require straightening the strip before it can be applied, or, if the strip tends to adhere to itself, curling back on itself may render the strip unusable. Excessively wide strips may also tend to extend beyond the intended treatment surface into areas which cause the strip to contact the connective soft tissue which joins the cheeks with the gingiva. If the strip extends into this u-shaped connective soft tissue region, it becomes more difficult for the strip to conform to the target treatment surfaces and remained adhered due to the differences in geometry and rates and directions of motion. The soft gingiva do not move whenever the mouth moves, while the cheek tissues do typically move when the mouth moves. This can cause the strip to be pulled in multiple directions, leading to loss of adhesion. Ultimately, the strip may be loosened and/or displaced from the target treatment surface or surfaces. Strips in the width range of 0.25 cm to 2 cm can work. Strips in the width range of 0.75 cm. to 1.5 cm appear to be optimal for polyolefin materials for this purpose. It should be understood that sizing is also a function of material choice for the strip of material. For posterior teeth, a preferred strip is sized and has sufficient stiffness to be handled by one hand while also being sized and be sufficiently flexible to be applied to the gumline of sensitive teeth without causing the strip to become dislodged.

Visual and Tactile Aspects of the Strips

Particularly on the posterior teeth, users may desire the ability to see the strip after the strip is applied, so they can visually confirm the strip placement. In some embodiments, the entire strip of material may be readily visible. For example, the strip of material may comprise opacifiers (such as mica, titanium dioxide, other inert opacifiers, and combinations thereof); colored strip material; translucent strip material; textured strip material; designs or artwork on the strip; or combinations thereof. In some embodiments, some portions or layers of the strip of material are readily visible, and others are not. For example, the portions of the strip intended to cover posterior teeth and adjacent gingiva may be readily visible. Portions of the strip intended to cover anterior teeth, particularly those teeth routinely visible to others, may be less visible (e.g., transparent or tooth-colored). As an alternative to visual confirmation, a strip of material with a texture enables consumers to confirm with their tongues that the strip is in place during the treatment time.

The strip of material may have a pastel color due to the inclusion of a food safe dye, or a blue color due to the inclusion of a blue food-safe dye, or both (e.g., in different portions or layers of the strip). Without being limited by theory, the use of pastel and/or blue hues may communicate to users that the product is gentler to the soft tissues than strips of other colors.

Desensitizing Oral Care Composition

Suitable desensitizing oral care compositions include a desensitizing agent, an adhesive-building polymer, a secondary structuring polymer, and water. As used herein, "oral care composition" means composition comprising a desensitizing agent, an adhesive-building polymer, a secondary structuring polymer, water, and, optionally, other components. An oral care composition may be homogenous, but does not have to be homogenous. The oral care composition components may be in the same phase or in separate phases, in a suspension, in laminates, dots, stripes, patterns, etc., as long as they interact sufficiently to sustainably provide the agent to the desired treatment location for a sufficient period of time.

The desensitizing oral care composition may optionally further contain other components such as additional oral care actives, such as fluoride salts, stannous salts, zinc salts, whitening agents, bluing agents, and combinations thereof; pH modifiers or buffers; humectants; plasticizers; flavors; sensates; rheology modifiers; TREK agonists; aesthetic particles; abrasive particles; or combinations thereof. TREK-1 channels control pain produced by mechanical stimulation. The TREK-1 channel has been linked to the TRPV1 pain response. TREK-1 potassium channel (TREK-1) agonists drive positive consumer perception from products containing them. The TREK-1 agonists further drive enhanced reduction in tooth sensitivity and/or oral discomfort, thus providing an oral comfort sensation. TREK-1 agonists include: L-carvone; gamma-dodecalactone; 4-ethyloctanoic acid; 2-Isopropyl-5-methyl-2-hexenal; 4-Methylnonanoic acid; trans-2-Decenal; Tributyl Phosphate; Dioctyl Adipate; Bis(2-ethyl hexyl) Phosphate; Spearmint oil; Synthetic Cassia; Methyl salicylate; Wintergreen oil; Thymol; Eugenol; and combinations thereof.

Delta Angle

Delta angle ($\delta$) is the phase lag between the applied and resulting stress and strain. The delta angle is related to the storage and loss moduli via equation 4. A completely elastic solid will have a delta angle of 0 degrees (°), that is, the stress and strains will be perfectly in phase. A completely viscous fluid will have a delta angle of 90°, that is, the stress and strains will be perfectly out of phase. Viscoelastic materials have delta angles between 0° and 90°.

$$G^* = G' + iG'' \quad \text{(Equation 3)}$$

$$\tan \delta = G''/G' \quad \text{(Equation 4)}$$

The desensitizing oral care compositions herein exhibit a delta angle value of less than or equal to about 35°, preferably less than or equal to about 32°, preferably less than or equal to about 30°, preferably less than 30°. In an example, the delta angle is further greater than or equal to about 5°, alternatively greater than or equal to about 10°, alternatively greater than or equal to about 12°.

Complex Modulus

Complex modulus (G*) is the combined storage modulus (G') and loss modulus (G'') according to equation 3. The complex modulus of viscoelastic compositions is often measured by applying a cyclic stress (or alternatively a cyclic strain) and measuring the resulting cyclic strain (or resulting cyclic stress). The oral care compositions have a complex modulus that is greater than or equal to 1700 multiplied by e (inverse log) raised to the power of (−0.05 multiplied by the delta angle value), see Equation 1. In an example, the complex modulus is equal to or greater than about 2100 multiplied by e to the power of (−0.05 multiplied by the Delta angle value), see Equation 2.

$$\text{Complex Modulus} \geq 1700 e^{(-0.05\ \text{Delta Angle})} \quad \text{(Equation 1)}$$

$$\text{Complex Modulus} \geq 2100 e^{(-0.05\ \text{Delta Angle})} \quad \text{(Equation 2)}$$

The viscoelastic properties of the oral care composition, such as the delta angle value and complex modulus of the composition, can be particularly important when the delivery system includes a release liner. If the desensitizing oral care composition fails to peel off of the release liner, or only peels off in part, the user will be unable to apply the strip of material and composition to the oral cavity or will experience limited efficacy. It is preferred that at least fifty percent (50%), alternatively at least 75%, alternatively at least 90%, or more, of the composition peels off the release liner when the strip of material and desensitizing oral care composition are about 3 cm long and are grasped and removed from the release liner by the fingers (such as a consumer would do when preparing to use the delivery system) at a rate of approximately 3 cm/sec.

The desensitizing oral care composition can be in the form of a viscous liquid, paste, gel, semi-solid, gummy, or other suitable form that can provide sufficient adhesion. Preferably, the composition is in the form of an aqueous gel. The composition may have a viscosity of from about 200 to about 1,000,000 cps at low shear rates (less than $1\ s^{-1}$). Preferably, the viscosity is from about 30,000 to about 800,000 cps and more preferably from about 100,000 to about 600,000 cps.

The desensitizing oral care composition may be applied to the strip of material by coating the entirety or a portion of the strip, and may be applied in a pattern (such as stripes, spots, geometric patterns, or other designs) or in layers, or in combinations thereof. For example, some portions of the strip may be coated with a substantially continuous, homogenous layer, and other portions of the strip may be coated in patterns and/or multiple layers. In some embodiments, the composition is applied to at least one side of the strip of material such that the strip of material includes from about 0.0005 to about 0.1 grams/cm² of the composition, alternatively from about 0.001 to about 0.05 grams/cm2 of the composition, or from 0.01 to 0.04 grams/cm². The composition may be applied to only one side of the strip of material.

It is also contemplated that the composition can be applied to the teeth and/or soft tissues of the oral cavity with an applicator (e.g. a brush, swab, or sponge). The composition can then optionally be covered with a piece or strip of material.

One example of a preferred adhesive oral care composition is one including CARBOPOL thickener, carboxymethylcellulose polymer, potassium oxalate, water, and glycerin.

Desensitizing Agent

The desensitizing oral care compositions disclosed may include a desensitizing agent. Exemplary desensitizing agents include oxalic acid, salts of oxalic acid, and mixtures thereof. Preferred salts of oxalic acid include the potassium salts of oxalic acid. A potassium salt of oxalic acid may be selected from dipotassium oxalate (CAS No. 127-96-8), potassium oxalate dehydrate (CAS No. 6100-20-5), potassium tetroxalate dehydrate (C4H7KO10), dipotassium oxalate monohydrate (CAS No. 6487-48-5, K2C2O4*H2O), and combinations thereof. Dipotassium oxalate monohydrate is commercially available in a water carrier as CAS No. 583-52-8 (equivalent to CAS No. 6487-48-5 plus CAS 7732-18-5 for the water carrier). In some embodiments, the desensitizing agent is selected from K2C2O4*H2O, K3H(C2O4)*2H2O, and mixtures thereof.

In some embodiments, the composition includes from about 0.01% to about 25%, alternatively from about 0.1% to about 25%, alternatively from about 0.05% to about 25%, alternatively from about 0.5% to about 15%, alternatively from about 1% to about 20%, alternatively from about 1% to about 10%, alternatively from about 1% to about 5%, alternatively from about 2% to about 5%, alternatively from about 2% to about 4%, by weight of the composition, of the desensitizing agent. In an example, the desensitizing oral care composition contains from about 2.5% to about 3.5%, by weight of the composition, of the desensitizing agent.

Additional compounds useful for reducing tooth sensitivity may be included in addition to the desensitizing agent. For example, the composition could further include a supplementary anti-sensitivity agent selected from other potassium salts, such as potassium nitrate, potassium chloride, potassium citrate, and combinations thereof; a stannous ion source such as stannous fluoride, stannous chloride, and combinations thereof; a strontium ion source such as a strontium salt; a zinc ion source such as a zinc salt; arginine; capsaicin; 2-hydroxyethyl methacrylate (HEMA); eugenol; a bioactive glass; arginines, for example, sodium arginine or arginic acid; fluoride ion sources; calcium ion sources; or any combination thereof. Additional compounds can include polymeric agents which can serve as both thickening agents and occluding agents—calcium-reactive polymers, e.g. alignates, work well for this purpose.

Water

The desensitizing oral care compositions may include at least 40% water, preferably at least 50%, more preferably at least 55%, by weight of the oral care composition, of water. The composition may contain from about 40% to about 95%, alternatively about 50% to about 95% water. This amount of water includes any free water that is added to the composition, plus that amount of water that is introduced with other materials.

Without being limited by theory, it has been observed that the level of water in the composition is important to achieve the desired dentinal tubule occlusion and resulting desensitizing benefit. Typically, a polymeric adhesive composition high in water content exhibits lower adhesiveness than the same composition with lower water. However, compositions with high water deliver oxalate much more effectively. In fact there is a decline in efficacy as the water content of the oxalate-containing composition declines. Further, without being limited by theory, lower water content can lead to the oxalate active being bound in the matrix and also result in a high counterflux of water out of the dentin, offsetting the delivery of the oxalate to the tubule. Generally, compositions containing less than 50% water do not effectively deliver oxalate as measured by the Pashley method, or, alternatively, the method of Example 3, which is a functional equivalent of the Pashley method. On the other hand, if the composition is too high in water, the composition may not be able to hold the strip in place for the desired contact wear time. Hence, there is a balance between the adhesiveness, water content and occlusion efficiency.

pH

In the literature, it is reported that some oxalate compositions work while others provide marginal efficacy at best. Upon examination of this inconsistent data, it is theorized that compositions with lower pH perform better than compositions with high pH. Some of the reports of poor performance may have been associated with compositions having an ineffective pH. However, given sufficient contact time, even higher pH compositions may provide good efficacy. Hence the pH of the composition will be considered when determining the required wear time, which in turn informs the desired properties of the adhesive matrix.

The pH of the composition may be less than about 8, alternatively from about 0.5 to about 8, alternatively from about 1 to about 7, alternatively from about 1.5 to about 6.0, alternatively from about 5.0 to about 5.4, alternatively about 5.2, alternatively less than about 4. For some deposition agents, a pH change of 0.1 units may be significant. In some embodiments, the pH of the composition may be about 1.1 to 6.9, or about 1.1 to about 3.0. The pH measurement should be taken after making the composition, before the product is packaged. A lower pH is generally more desirable, with lower pH most helpful with certain salts and/or reduced contact time between the strip and the sensitive tissues.

pH Adjusting Agent

The desensitizing compositions may optionally include a pH adjusting agent to improve the storage stability of the composition or to make the substance gentle for oral hard and soft tissues, or both. These pH adjusting agents, or buffers, if used, can be any material which is suitable to adjust the pH of the oral care composition. Exemplary pH adjusting agents include sodium bicarbonate, sodium phosphate, sodium hydroxide, ammonium hydroxide, sodium stannate, triethanolamine, citric acid, hydrochloric acid, sodium citrate, silica, and combinations thereof. When used, the pH adjusting agents are generally present in an amount of from about 0.001% to about 10%, preferably from about 0.05% to about 5%, by weight of the oral care composition.

Polymers

The desensitizing oral care compositions herein include an adhesive-building polymer and a secondary structuring polymer.

Without being limited by theory, it has surprisingly been found that a balanced combination of an adhesive polymer and a secondary structuring polymer further in combination with the appropriate amount of water and desensitizing active can be established by selecting the compositional elements according to those capable of meeting the preferred range of rheological conditions. Compositions of relatively high water content are typically not very adhesive, and may not provide suitable adhesion of the strip to sensitive teeth or tissues. Underhydrated polymers of the same type may be more adhesive, but may not be stable during storage or may delay the release of desensitizing agents from the polymer. Using a combination of an adhesive polymer and a secondary structuring polymer resolves this dilemma.

Further without being limited by theory, it has been surprisingly found that by selectively balancing the amount and grade of at least two polymers, each having the capability to hydrogen bond and, the first, an adhesive thickening polymer having a higher density of carboxyl groups than a second structuring polymer, that targeted delivery of the desensitizing agent to the oral cavity can be made for a desirable period of time.

Adhesive-Building Polymer

The desensitizing oral care compositions may include from about 0.1% to about 30%, by weight of the composition, of an adhesive-building polymer. The compositions may contain from about 0.5% to about 20%, alternatively from about 0.5% to about 10%, alternatively from about 1% to about 5%, alternatively from about 2.25% to about 10%, alternatively from about 2.25% to about 6%, by weight of the composition, of the adhesive-building polymer.

As used herein, "adhesive-building polymer" refers to the general class of polymers capable of modifying the viscosity of a composition as well as providing adhesive properties, preferably muco-adhesive properties, to the composition, either alone or in combination with other composition components. Adhesion to both hard and soft oral tissues (at least temporarily) is desirable. Such polymers are capable of hydrogen bonding, contain polar or charged groups and are hydrophilic. One of ordinary skill will understand that the level of adhesive properties can be varied to provide adhesion for longer or shorter periods of time in the oral cavity, depending on the desired application time. Some adhesive polymers, like PVP, may also require polyols to help build adhesiveness.

The composition may be coated onto a strip of material and may be capable of sufficiently holding the strip and the composition against the hard and/or soft tissues of the oral cavity for a period of time. That period of time may be at least 0.5 minutes, alternatively at least 5 minutes, alternatively at least 10 minutes, alternatively at least 15 minutes. The period of time may be from about 5 minutes to about 2 hours, alternatively from about 5 minutes to about 1 hour, alternatively from about 10 minutes to about 30 minutes, alternatively overnight (e.g., 6-12 hours, or 6-10 hours, or approximately 8 hours).

Adhesive-building polymers useful herein include polycarboxylic acids selected from carboxypolymethylene resins.

Carboxypolymethylene is a slightly acidic vinyl polymer with active carboxyl groups. Carboxypolymethylene resins useful herein include those commercially available under the trade name CARBOPOL. CARBOPOL is the trade name for a general class of high molecular weight homo and co-polymers of acrylic acid crosslinked with a polyalkenyl polyether. Such polymers are commercially available from Lubrizol (Ohio, USA). Pharmaceutical grade carboxypolymethylene resins are particularly useful herein.

An example adhesive polymer for use herein is CARBOPOL 956, commercially available from Lubrizol, and having a viscosity as measured on a Brookfield RVT at 20 rpm, neutralized to pH 7.3-7.8 with 0.5% wt % mucilage and a spindle #6 of from 20,7000 to 41,300 at 25° C. Other examples of commercially available materials useful herein include CARBOPOL 980 NF, CARBOPOL 974P NF, CARBOPOL 984 EP, CARBOPOL ULTREZ 10 NF, CARBOPOL 971P NF, and combinations thereof.

In an example, the adhesive-building polymer is selected from high molecular weight homo and co-polymers of acrylic acid crosslinked with a polyalkenyl polyether, and mixtures thereof.

Other adhesive-building polymers useful herein include the EUDRAGIT series of polymethacrylate-based copolymers. The series includes anionic, cationic, and neutral copolymers based on methacrylic acid and methacrylic/acrylic esters or their derivatives. Such polymers are commercially available from Evonik (Essen, Germany).

Other examples of adhesive-building polymers useful herein include PVP, polymers having a polycarboxylated ethylene backbone (e.g. the GANTREZ, ACUSOL, or SOKALAN series of polymers), poly(2-ethyl-2-oxazoline), polyacrylamide, copolymers with acrylamide, pectin, proteins, high molecular weight polyethylene glycols (e.g. POLYOX, AQUAZOL), and mixtures thereof.

The GANTREZ series of polymers are copolymers of maleic anhydride with methyl vinyl ether having a molecular weight (M.W.) of about 30,000 to about 1,000,000. These copolymers are available for example as Gantrez AN 139 (M.W. 500,000), AN 119 (M.W. 250,000) and S-97 Pharmaceutical Grade (M.W. 70,000), from Ashland Chemicals (Kentucky, USA).

The ACUSOL and the SOKALAN series of polymers include homopolymers of acrylic acid and copolymers of maleic acid and acrylic acid or methacrylic. Examples are 0:1000 to 1000:0 copolymers of maleic acid with acrylic acid having a molecular weight (M.W.) of about 2,000 to about 1,000,000. These copolymers are commercially available as Acusol 445 and 445N, Acusol 531, Acusol 463, Acusol 448, Acusol 460, Acusol 465, Acusol 497, Acusol 490 from Dow Chemicals (Michigan, USA) and as Sokalan CP 5, Sokalan CP 7, Sokalan CP 45, and Sokalan CP 12 S from BASF (New Jersey, USA).

Other examples of adhesive-building polymers useful herein include ethylene oxide polymers, homopolymers or mixtures of ethylene oxide polymers of varying molecular weight ranging from about 10,000 Daltons up to about 10,000,000 Daltons, and preferably in the range of about 100,000 to about 1,500,000 Daltons. Polyethylene oxide in the molecular weight range of 10,000 to 1,000,000 Daltons is available from the Dow Chemical Company (Michigan, USA) under the trade name POLYOX.

Other examples of adhesive-building polymers useful herein include PVP, poly(2-ethyl-2-oxazoline), polyacrylamide, copolymers with acrylamide, pectin, proteins, high molecular weight polyethylene glycols (e.g. AQUAZOL from PCI, Inc. Arizona, USA), and mixtures thereof.

One class of polymers that is not recommended for use herein is the block polypropylene oxide, polyethylene oxide copolymers sold under the trade name PLURONICS by BASF (New Jersey, USA).

Secondary Structuring Polymer

The desensitizing oral care compositions may include a water-soluble, water swellable or water hydratable secondary structuring polymer. The compositions contain from about 0.5% to about 40%, by weight of the composition, of the secondary structuring polymer. The compositions may contain from about 1% to about 20%, alternatively from about 1% to about 10%, alternatively from about 2% to about 6%, alternatively from about 2.5% to about 5.5%, by weight of the composition, of the secondary structuring polymer.

"Secondary structuring polymer" as used herein refers to a water-soluble, water swellable or water hydratable polymer that, when used in the compositions of the present invention, is capable of providing the delta angle value parameter needed and/or providing viscoelastic properties suitable for the benefits desired such as reducing gel flow off the strip, or releasing from a release liner or other applicator in one piece (or at least partially releasing).

The secondary structuring polymer may be selected from polycarboxylates, carboxylate-substituted polymers, and mixtures thereof.

Examples of secondary structuring polymers useful herein include polysaccharides. An example secondary structuring polymer is a carboxymethyl polysaccharide. The secondary structuring polymer may be selected from cellulosic polymers, preferably derivatized cellulosic polymers, preferably carboxylate derivatized cellulose, preferably carboxymethylcellulose.

The secondary structuring polymer may be selected from carboxymethylcellulose, dextran, starch, pectins, and mixtures thereof. The secondary structuring polymer can be a sodium carboxymethylcellulose.

The secondary structuring polymer can be selected from hydroxyethylcellulose, hydroxypropylcellulose, hydroxypropylmethylcellulose, methylcellulose, ethylcellulose, cellulose, sodium carboxymethylcellulose, corn starch, and mixtures thereof.

The carboxymethylcellulose can be selected front those having from about 0.5 to about 1.5 degrees of substitution, preferably about 0.65 to about 0.75 degrees of substitution. In an example, the carboxymethylcellulose has a viscosity in a 2% solution with water of from about 100 to about 1500 milliPascals (mPas), alternatively from about 100 to about 900 mPas, alternatively from about 200 to about 800 mPas. Preferably the secondary structuring polymer is food grade. Preferably the carboxymethylcellulose is of smooth type.

Examples of specific grades of useful carboxymethylcellulose include AQUALON 7M8SF, commercially available from Hercules (Delaware, USA), having a viscosity of a 2% solution in water of 200-800 mPas and a degree of substitution of from about 0.65 to about 0.9. The overall AQUALON 7M series has a viscosity in a 2% solution of water of from about 100 to about 1800 mPas with a degree of substitution of from about 0.65 to about 0.9 and the AQUALON 7H series has a viscosity in 1% solution of water from about 1000 to about 6000 mPas, also with a degree of substitution of from about 0.65 to about 0.9. The overall AQUALON 9H food grade series of carboxymethylcellulose has a viscosity of from 2500-6000 milliPascals, and a degree of substitution of from about 0.80 to about 0.95. A combination of polymers from within or between the AQUALON 7H and AQUALON 9H series may be used.

Optional Additional Thickener

In addition to the adhesive-building polymer and secondary structuring polymer, the compositions herein may further include an additional thickener that is compatible with the polymers, desensitizing agent, and other components. Examples of additional thickeners useful herein include gums, resins, alginates, carrageenan, gelatin, algin, chitosan, polyamines, polyquaternary compounds, and mixtures thereof. Gums useful herein include xanthan gum, karaya gum, guar gum, gum arabic, gum tragacanth, and mixtures thereof. Polyols such as sorbitol and glycerin may help build the thickness of adhesive-building polymers. A preferred additional thickener is xanthan gum.

Plasticizer/Humectant

The desensitizing compositions may include from about 1% to about 40%, by weight of the composition, of a humectant, sometimes referred to in the literature as a plasticizer. The composition may contain from about 5% to about 40%, alternatively from about 10% to about 40%, alternatively from about 20% to about 35%, alternatively from about 25% to about 35%, alternatively about 30%, by weight of the composition, of a humectant.

Humectants useful herein include, for example, glycols such as propylene glycol, polyethylene glycol, polyhydric alcohols such as glycerin and sorbitol and glycerol esters such as glycerol triacetate. Glycerin can be used as well as propylene glycol or polyethylene glycol such as is available from Union Carbide Corporation as their series of CARBOWAX materials that range in molecular weight from 200 to 600 Daltons. Other plasticizers include cellulose esters, sebacate esters, castor oil, tricresyl phosphate, and pthalate adipate. The plasticizer can be glycerin.

Other Oral Care Actives/Materials

In addition to the desensitizing agent, other oral care actives (or materials) may be included in the desensitizing compositions herein. Suitable oral care actives generally include any material that is generally considered as safe for use in the oral cavity that provides beneficial changes to the oral cavity, and in an example, improves the condition of the oral surfaces the oral care composition contacts.

Optional materials include, for example, flavoring agents, dyes (including hueing dyes such as those in the blue or violet spectrum), sweetening agents, xylitol, opacifiers, and coloring agents. Flavorants which may also function as TREK agonists may be preferred for added desensitizing activity; these include Spearmint oil, Wintergreen oil, thymol, eugenol, and combinations thereof.

Optional oral care actives useful herein include many of the actives previously disclosed in the art such as teeth whitening actives, phosphates (for anti-tartar benefits), fluoride ion sources, antimicrobial agents, anti-inflammatory agents, nutrients, enzymes, anti-fungals, antibiotics, analgesic agents, antioxidants, H-2 antagonists, and combinations thereof. A more extensive description of such actives may be found in U.S. Pat. No. 6,136,297 assigned to the Procter & Gamble Company.

In an example, the desensitizing composition further includes a whitening active. Whitening actives useful herein include peroxides, metal chlorites, perborates, percarbonates, peroxyacids, and combination thereof. Suitable peroxide compounds include hydrogen peroxide, calcium peroxide, carbamide peroxide, and mixtures thereof. Suitable metal chlorites include calcium chlorite, barium chlorite, magnesium chlorite, lithium chlorite, sodium chlorite, and potassium chlorite. Additional whitening actives include hypochlorite and chlorine dioxide.

Composition Applied to the Strip of Material

The desensitizing composition can be applied to at least one side of the strip of material. The strip of material may be manufactured and then the composition applied (such as by spray-drying and/or extrusion), and/or the composition may be applied during the manufacture of the strip of material, such as by co-extrusion. The composition may be applied to the oral surface and the strip of material applied over the composition.

The amount of composition applied to the strip of material or oral surface depends upon the size and capacity of the material, concentration of the active, and the desired contact time in the oral cavity. Generally, less than about 1 gram of oral care composition is required. Preferably, from about 0.001 grams to about 0.5 grams, and more preferably from about 0.01 gram to about 0.4 grams of the oral care composition is used. The amount of oral care composition per square cm of material is less than about 0.5 grams/cm$^2$, preferably from about 0.0005 to about 0.1 grams/cm$^2$, and more preferably from about 0.001 grams/cm$^2$ to about 0.04 grams/cm$^2$.

Release Liner

The delivery systems herein optionally include a release liner. The release liner may be a fluoropolymer coated polypropylene film. Examples of such a film include the SCOTCHPACK 9741 RELEASE LINER commercially available from 3M (Minnesota, USA). Preferably, there is a minimum border of the release liner available as "overage" to the strip of material and/or composition, to allow the user to grab onto the strip and pull the strip off the release liner before use.

Figure 4:
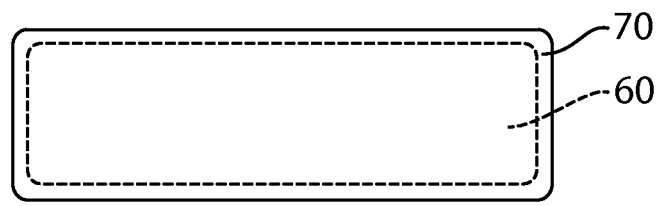
FIG. 4 is a schematic view of an exemplary release liner.
Figure 5:
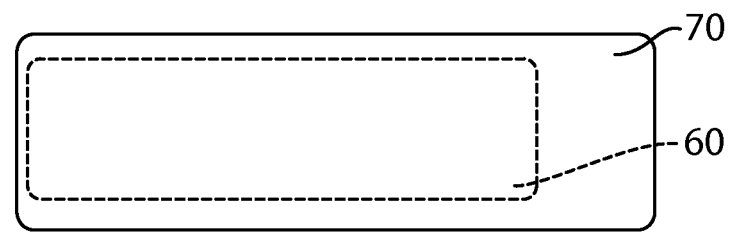
FIG. 5 is a schematic view of an exemplary release liner.
Figure 6:
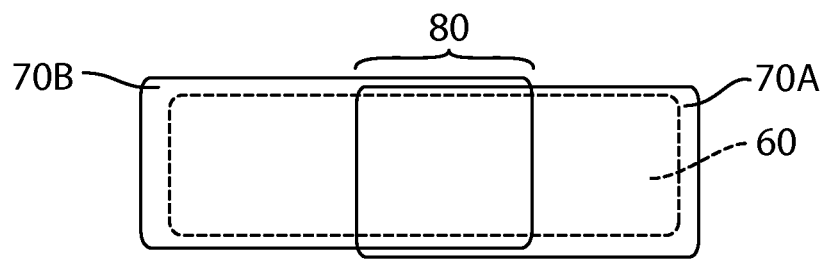
FIG. 6 is a schematic view of an exemplary release liner.

The release liner may be formed from any material which exhibits less affinity for the desensitizing composition than the desensitizing composition exhibits for itself and for the strip of material. The release liner preferably comprises a relatively rigid sheet of material (compared to the strip of material) such as polypropylene, paper, polyester, or other material which is then coated with a non-stick type material or sacrificial release coating. The release liner material may be coated with wax, silicone, teflon, fluoropolymers, or other non-stick type materials. A preferred release liner is Scotchpak®, produced by 3M. As shown in FIGS. 4-6, the release liner 70 may be cut to substantially the same size and shape as the strip of material 60 or the release liner 70 may be cut larger than the strip of material 60 to provide a readily accessible means for separating the material from the strip. The release liner may be formed from a brittle material which cracks when the strip is flexed or from multiple pieces of material or a scored piece of material. Alternately, the release liner 70 may be in two overlapping pieces, 70A and 70B, with overlapping area 80, such as a typical adhesive strip bandage design. A further description of materials suitable as release agents is found in Kirk-Othmer Encyclopedia of Chemical Technology, Fourth Edition, Volume 21, pp. 207-218, incorporated herein by reference.

Preferably, a release liner is used to present the sensitivity treatment strip to the consumers. The adhesive matrix coated strip is placed on the release liner such that the adhesive matrix is between the strip of material and the release liner. When removing the strip an adhesive matrix from the release liner, it is preferable to have most or all of the adhesive matrix remain with the strip of material. In order for this to be the case, the adhesive matrix should have more affinity for the strip of material than the release liner. In addition, the adhesive matrix must have sufficient internal strength or cohesion such that the gel does not shear leaving some adhesive matrix on the strip and some of the release liner. Without being limited by theory, it was surprisingly learned that when using just one adhesive-building polymer, such as e.g., CARBOPOL, the strip of material and composition may not sufficiently release off the release liner. Using just a secondary structuring polymer, such as, e.g., CMC, the product releases, but may lack sufficient adhesion in-vivo. An adhesive-building polymer and a structuring polymer combined may be needed to provide an acceptable balance of release and adhesion.

Physical stability of the composition on the strip of material once applied to the release liner can also be important. Specifically, once the strip of material and composition are applied to the release liner, it is desirable to have the adhesive matrix remain within the perimeter of the strip, meaning, e.g. it does not flow significantly outside the boundaries of the strip. Flowing outside the boundaries of the strip may create an undesirable situation with respect to the packaging of the strip, for example in a pouch. In this case, the gel which has flowed outside of the perimeter of the strip can adhere the strip to the inside of the pouch making it difficult to remove before use. With other packaging such as, e.g., a tray and cover, this may be of less concern.

Packaging

The delivery system may be packaged in any package suitable for providing a moisture barrier. One example is a foil laminate pouch, another is a plastic tray.

Methods of Use

Methods of using the desensitizing delivery system set forth herein to treat the oral cavity (or portions thereof) before or after the use of a whitening delivery system (such as a commercially available whitening strip product like CREST WHITESTRIPS) are also contemplated herein.

In practicing the present invention, a strip of material may be applied to the desired oral surface by the wearer. The side of the material facing the oral surface is at least the side wherein the composition herein is applied. This oral care composition provides a vehicle for the active as well as tackiness between the oral surfaces and the strip of material, holding the strip of material in place for extended periods of time. The period over which the strip of material is used may be, for example, from about one to about thirty minutes.

The strip of material may readily conform to the oral care surface by lightly pressing it there against, e.g., under light to moderate finger pressure. The strip of material is easily removed by the wearer by peeling it off using a finger or fingernail. Preferably each successive treatment uses a fresh strip of material.

In the situation were the oral care surface is the surface of teeth, it may be unnecessary to prepare the teeth surface before applying the delivery system of the present invention. For example, the wearer may or may not choose to brush his teeth or rinse his mouth before applying the delivery system. The surfaces of the teeth are not required to be dried or to be excessively wet with saliva or water before the strip of material is applied.

When the wearer removes the strip of material from the oral surface, there may be a residual amount of oral care composition remaining on the surface. The amount residual oral care composition, however, may not be great in embodiments where the oral care composition has affinity for both the strip of material (e.g., adhesion to the delivery strip) and for itself (e.g., cohesion). Any residual oral care composition may be easily removed by wiping, brushing or rinsing the oral surface.

The delivery system herein may optionally be applied with two fingers to the oral surface in need of treatment. The delivery system may be allowed to remain in place for at least five minutes. The delivery system may be applied to cover at least a portion of a tooth and at least a portion of the adjoining soft tissue (gum) area.

EXAMPLES

Testing Methodology

Complex Modulus and Delta Angle

To measure the complex modulus (G*) and delta angle of a composition according to the present invention, the following procedure is used. An Advanced Rheometer 2000 (AR2000, TA Instruments, New Castle, Del.) equipped with a stainless steel cone and plate fixture is provided. The cone and plate diameter used is 40 mm with a cone angle of 2 degrees. The testing is conducted at room temperature, approximately 25 degrees C. After the fixture is installed and the instrument initialized, an excess amount of the bulk composition is placed on the bottom plate and the cone is lowered into the composition to a final gap of 0.048 mm Excess composition will extrude from the gap between the cone and plate and must be removed without pulling material from out of the gap. Approximately 0.6 mL of the composition remains between the cone and plate. The instrument is set to perform oscillatory strain cycles with the following parameters:

Duration of Run: 30 minutes
Applied Strain: 1%
Frequency: 1 Hz
Sample Points per run: 15

The data is analyzed using TA Instrument's software, TA Rheology Advantage Data Analysis version 5.7.0. The software is used to generate plots of either complex modulus or delta angle versus time and the mean value for the period 1 to 30 minutes is determined.

To determine the low shear viscosity, the same rheometer, rheometer tooling, gap, and software are used. The procedure for measuring the low shear viscosity is as follows: After sample loading/trimming, condition sample at 25° C. for 10 minutes. Conduct a steady state Stress ramp from 2-200 Pa at 25° (Log mode, 10 points/decade, 5% tolerance). Then condition at 25° C. for 2 minutes. Then Continuous Ramp shear rate from 0.1-100 sec$^{-1}$ (Log mode, 5 minute test, 10 points/decade). Then plot Log Viscosity (y axis) vs. Log Shear Rate (x axis). Visually assess plot and determine viscosity in the low shear rate plateau region.

Example 1

Compositions according to the present invention were made according to the formulations set forth in Tables 1A through 1D, below.

Comparative Examples were made according to the formulations set forth in Tables 2A through 2B, below.

As may be seen in the results shown in Tables 1A through 1B=D, when compared to the results presented in Tables 2A and 2B, and graphically represented in FIG. 1 attached herein, compositions according to the present invention, when applied to a strip of material and a release liner were found to provide sufficient adherence in-vivo, refrain from significant gel flow off the strip during storage, and release the majority of the oral care composition gel from the release liner.

Examples of desensitizing compositions according to the present invention are found below in Tables 1A, 1B, 1C, and 1D. Comparative examples of desensitizing compositions are found in Tables 2A and 2B. The compositions were compounded using either a Ross double planetary mixer LDM-2 or Ross double planetary mixer DPM-40. Glycerin was weighed and added to a clean Ross mix tank. Water was weighed and added to a separate stainless steel mix tank equipped with a lightning mixer and 4" diameter turbine mixing blade. The carboxymethyl cellulose and the CARBOPOL were weighed and added to a clean plastic polyethylene bucket. The lid was applied to the bucket and the powders were rotated by hand to blend the powders together for 10 minutes. The potassium sorbate, potassium benzoate and potassium oxalate were weighed and added to the water in the stainless steel mixing tank. The lightning mixer was then used to completely dissolve the added salts. The sodium hydroxide was weighed and added to the potassium sorbate/sodium benzoate/potassium oxalate solution in the stainless steel mix tank. The solution was then mixed until clear. The blended carboxymethyl cellulose and CARBOPOL powder mix was carefully added to the glycerin by hand adding to cover the surface of the glycerin uniformly in the Ross mix tank. The Ross mixer was started and ran at a speed setting of 5 for 30 minutes. The solution from the stainless steel tank was then added to the Ross mixer and mixing continued for 45 minutes at a speed setting of 5. After this mixing session, the composition was checked for visible lumps. If lumps were present, the composition was mixed for an additional 20 minutes at a speed setting of 5.

Once the compounding of the composition is complete, strip-type delivery systems were made by slot coating the composition onto a sheet of release liner made of fluoropolymer coated polypropylene film sold under the brand name SCOTCHPACK 9741 RELEASE LINER (commercially available from 3M (Minnesota, USA)) and then combined with a polyethylene film material, an HDPE/LDPE blend polyethylene film (commercially available from Clopay (Cincinnati, USA) as embossed polyethylene film—32 GSM Sof-flex) using a continuous lamination process. This resulting laminate was then run through rotary kiss cutting dies to cut the strip shape to 1 cm×3 cm. The polyethylene material outside of the strip perimeter was removed and the resultant release liner with 1 cm×3 cm strip spaced out on the web was cut into individual release liners measuring 3 cm×9 cm. The individual release liners with strips were placed into foil laminate pouches and sealed with heat.

The resulting delivery systems were tested for release off the release liner and gel flow and the Complex Modulus and Delta were measured and calculated pursuant to the methods set forth herein. Some products were further tested for in vivo adhesion and the results included below. To determine release off the liner, the strip was removed from the foil laminate pouch and the strip and laminated composition were grasped between two fingers and pulled from the release liner at a rate of approximately 3 cm/sec. The percentage amount of composition remaining on the release liner was visually analyzed and recorded. In vivo adhesion was determined by a wear panel.

The delivery systems with the compositions shown in Table 1A, 1B, 1C, and 1D are according to the invention set forth herein. As may be seen by the data tabulated in the Tables below, compositions 1a through 1t were found to perform acceptably in all categories tested. Those in 1m and 1n as well as 1p through 1t include an optional additional thickener, xanthan gum.

Comparative delivery systems are shown and the data associated therewith are tabulated below in Tables 2A, 2B. Such comparative delivery systems, where tested, exhibited at least one unacceptable characteristic that make them less suitable for treating dentinal hypersensitivity.

FIG. 1 plots the Complex Modulus versus the Delta value for the compositions shown in Tables 1A, 1B, 1C, 1D as well as 2A and 2B. As may be seen in FIG. 1, the example formulations in 1A, 1B, 1C and 1D meet Equation 1 (indicated by the solid black line), while 2A and 2B fall outside the desired relationship. Equation 2 is shown as a dotted black line.

TABLE 1A

Desensitizing Oral Care Compositions

| Ingredient | 1a Wt. % | 1b Wt. % | 1c Wt. % | 1d Wt. % | 1e Wt. % |
|---|---|---|---|---|---|
| Carboxymethyl Cellulose 7M8SF | 5.0 | 5.0 | 4.5 | 4.5 | 4.0 |
| Glycerin USP (99.7) | 31.86 | 31.86 | 31.86 | 31.86 | 31.86 |
| CARBOPOL 956 | 1.0 | 1.0 | 2.5 | 2.5 | 2.5 |
| Sodium Benzoate, NF FCC | 0.50 | 0.5 | 0.5 | 0.5 | 0.5 |
| Potassium Sorbate | 0.20 | 0.2 | 0.2 | 0.2 | 0.2 |
| Sodium Hydroxide Solution 50 | 0.25 | 0.25 | 1.1 | 1.05 | 1.0 |
| Potassium Oxalate Monohydrate, ACS | 3.14 | 3.14 | 3.14 | 3.14 | 3.14 |
| Purified Water USP | 58.05 | 58.05 | 56.2 | 56.25 | 56.8 |
| TEST RESULTS: | | | | | |
| Complex Modulus (G*) | 709 | 860 | 1085 | 908 | 883 |
| Delta (Degrees) | 27.2 | 20.2 | 23.8 | 22.7 | 24.2 |
| $1700\, e^{(-0.05\, Delta\, Angle)}$ (Equation 1) | 436.3233 | 619.1723 | 517.1761 | 546.4176 | 506.9354 |
| $2100\, e^{(-0.05\, Delta\, Angle)}$ (Equation 2) | 538.9876 | 764.8599 | 638.8647 | 674.9865 | 626.2143 |
| Release from Release Liner (%) | 100 | 100 | 95 | * | 100 |
| Gel Flow off strip | No | * | No | No | No |
| Adheres in-vivo | Yes | * | Yes | Yes | Yes |

Carboxymethyl Cellulose 7M8SF, 9H, and 7H are part of the AQUALON series commercially available from Hercules.
CARBOPOL 956 is commercially available from Lubrizol.
*Data point not collected for sample.

TABLE 1B

Desensitizing Oral Care Compositions

| Ingredient | 1f Wt. % | 1g Wt. % | 1h Wt. % | 1i Wt. % | 1j Wt. % |
|---|---|---|---|---|---|
| Carboxymethyl Cellulose 7M8SF | 4.5 | 4.5 | 4.5 | 4.5 | 4.5 |
| Glycerin USP (99.7) | 31.86 | 31.86 | 31.86 | 31.86 | 31.86 |
| CARBOPOL 956 | 2.0 | 2.0 | 2.0 | 2.0 | 2.0 |
| Sodium Benzoate, NF FCC | 0.5 | 0.5 | 0.5 | 0.5 | 0.5 |
| Potassium Sorbate | 0.2 | 0.2 | 0.2 | 0.2 | 0.2 |
| Sodium Hydroxide Solution 50 | 0.75 | 0.75 | 0.75 | 0.75 | 0.75 |
| Potassium Oxalate Monohydrate, ACS | 3.14 | 3.14 | 3.14 | 3.14 | 3.14 |
| Purified Water USP | 57.05 | 57.05 | 57.05 | 57.05 | 57.05 |
| TEST RESULTS: | | | | | |
| Complex Modulus (G*) | 855.4 | 874 | 1093 | 1108 | 1049 |
| Delta (Degrees) | 25.2 | 25.6 | 18.4 | 18.5 | 19.2 |
| $1700\, e^{(-0.05\, Delta\, Angle)}$ (Equation 1) | 482.2118 | 472.6634 | 677.4824 | 674.1034 | 650.9179 |
| $2100\, e^{(-0.05\, Delta\, Angle)}$ (Equation 2) | 595.6735 | 583.8783 | 836.89 | 832.716 | 804.0751 |

TABLE 1B-continued

Desensitizing Oral Care Compositions

| Ingredient | 1f Wt. % | 1g Wt. % | 1h Wt. % | 1i Wt. % | 1j Wt. % |
|---|---|---|---|---|---|
| Release from Release Liner (%) | 100 | 100 | 100 | 100 | 100 |
| Gel Flow off strip | No | No | * | * | * |
| Adheres in-vivo | Yes | Yes | * | * | * |

Carboxymethyl Cellulose 7M8SF, 9H, and 7H are part of the AQUALON series commercially available from Hercules.
CARBOPOL 956 is commercially available from Lubrizol.
*Data point not collected for sample.

TABLE 1C

Desensitizing Oral Care Compositions

| Ingredient | 1k Wt. % | 1l Wt. % | 1m Wt. % | 1n Wt. % | 1o Wt. % |
|---|---|---|---|---|---|
| Carboxymethyl Cellulose 7M8SF | 5.0 | 5.0 | 4.0 | 2.5 | 5.0 |
| Glycerin USP 99.7 | 31.86 | 31.86 | 31.86 | 31.86 | 31.86 |
| CARBOPOL 956 | 1 | 1.0 | 1.0 | 2.5 | 1.5 |
| Xanthan Gum, NF | | | 1.0 | 2.5 | |
| Sodium Benzoate, NF FCC | 0.5 | 0.5 | 0.5 | 0.5 | 0.5 |
| Potassium Sorbate | 0.2 | 0.2 | 0.2 | 0.2 | 0.2 |
| Sodium Hydroxide Solution 50 | .25 | 0.25 | 0.25 | 1.2 | 0.5 |
| Potassium Oxalate Monohydrate, ACS | 3.14 | 3.14 | 3.14 | 3.14 | 3.14 |
| Purified Water USP | 58.05 | 58.05 | 58.05 | 55.6 | 57.3 |
| TEST RESULTS: | | | | | |
| Complex Modulus (G*) | 1087 | 2912 | 664 | 1357 | 993 |
| Delta (Degrees) | 27.9 | 12.6 | 24.4 | 16.3 | 20.8 |
| 1700 e $^{(-0.05\ Delta\ Angle)}$ (Equation 1) | 421.3162 | 905.4061 | 501.8913 | 752.4869 | 600.873 |
| 2100 e $^{(-0.05\ Delta\ Angle)}$ (Equation 2) | 520.4494 | 1118.443 | 619.9834 | 929.5426 | 742.2548 |
| Release from Release Liner (%) | No data | 100 | 100 | 98 | 100 |
| Gel Flow off Strip | No | No | No | No | * |
| Adheres in-vivo | Poorly | Poorly | * | * | * |

Carboxymethyl Cellulose 7M8SF, 9H, and 7H are part of the AQUALON series commercially available from Hercules.
CARBOPOL 956 is commercially available from Lubrizol.
*Data point not collected for sample.

TABLE 1D

Desensitizing Oral Care Compositions

| Ingredient | 1p Wt. % | 1q Wt. % | 1r Wt. % | 1s Wt. % | 1t Wt. % | 1u Wt. % |
|---|---|---|---|---|---|---|
| Carboxymethyl Cellulose 7M8SF | 3.0 | 3.0 | 3.0 | 3.5 | 3.5 | 5.0 |
| Glycerin USP 99.7 | 31.86 | 31.86 | 31.86 | 31.86 | 31.86 | 31.86 |
| CARBOPOL 956 | 2.0 | 2.0 | 2.5 | 2.5 | 2.5 | 5 |
| Xanthan Gum, NF | 1.5 | 2.0 | 1.0 | 1.0 | 1.0 | |
| Sodium Benzoate, NF FCC | 0.5 | 0.5 | 0.5 | 0.5 | 0.5 | 0.5 |
| Potassium Sorbate | 0.2 | 0.2 | 0.2 | 0.2 | 0.2 | 0.2 |
| Sodium Hydroxide Solution 50 | 0.75 | 0.75 | 1.0 | 1.0 | 1.05 | |
| Potassium Oxalate Monohydrate, ACS | 3.14 | 3.14 | 3.14 | 3.14 | 3.14 | 3.14 |
| Purified Water USP | 56.7 | 56.55 | 56.8 | 56.3 | 56.25 | 54.3 |
| TEST RESULTS: | | | | | | |
| Complex Modulus (G*) | 794 | 920 | 877 | 1041 | 849 | 3131 |

TABLE 1D-continued

Desensitizing Oral Care Compositions

| | 1p Wt. % | 1q Wt. % | 1r Wt. % | 1s Wt. % | 1t Wt. % | 1u Wt. % |
|---|---|---|---|---|---|---|
| Delta (Degrees) | 21.6 | 20.6 | 21 | 21.4 | 20.7 | 16.3 |
| $1700\ e^{(-0.05\ Delta\ Angle)}$ (Equation 1) | 577.3124 | 606.9118 | 594.8942 | 583.1145 | 603.8848 | 752.4869 |
| $2100\ e^{(-0.05\ Delta\ Angle)}$ (Equation 2) | 713.1506 | 749.7146 | 734.8693 | 720.3179 | 745.9754 | 929.5426 |
| Release from Release Liner (% Released) | 95 | 95 | 100 | 100 | 100 | 99 |
| Gel Flow off Strip | No | No | No | No | No | * |
| Adheres in-vivo | Yes | Yes | Yes | Yes | Yes | * |

Carboxymethyl Cellulose 7M8SF, 9H, and 7H are part of the AQUALON series commercially available from Hercules.
CARBOPOL 956 is commercially available from Lubrizol.

TABLE 2A

Comparative Desensitizing Oral Care Compositions

| Ingredient | 2a Wt. % | 2b Wt. % | 2c Wt. % | 2d Wt. % | 2e Wt. % |
|---|---|---|---|---|---|
| Carboxymethyl Cellulose 7M8SF | | 2.5 | 2.5 | 1 | 2 |
| Glycerin USP 99.7 | 31.86 | 31.86 | 31.86 | 31.86 | 31.86 |
| CARBOPOL 956 | 5.0 | 2.5 | 2.5 | 1.0 | 3.0 |
| Sodium Benzoate, NF FCC | 0.5 | 0.5 | 0.5 | 0.5 | 0.5 |
| Potassium Sorbate | 0.2 | 0.2 | 0.2 | 0.2 | 0.2 |
| Potassium Oxalate Monohydrate, ACS | 3.14 | 3.14 | 3.14 | 3.14 | 3.14 |
| Purified Water USP | 57.3 | 59.3 | 59.3 | 62.3 | 59.3 |
| TEST RESULTS: | | | | | |
| Complex Modulus (G*) | 1148 | 422 | 486 | 25 | 501 |
| Delta (Degrees) | 6.1 | 25.4 | 23.7 | 33 | 21.8 |
| $1700\ e^{(-0.05\ Delta\ Angle)}$ (Equation 1) | 1253.11 | 477.4138 | 519.7685 | 326.4848 | 571.568 |
| $2100\ e^{(-0.05\ Delta\ Angle)}$ (Equation 2) | 1547.959 | 589.7464 | 642.067 | 403.3048 | 706.0546 |
| Release from Release Liner (% Released) | 20 | 50 | 75 | 0 | 30 |
| Gel Flow off Strip | * | * | * | * | * |
| Adheres in-vivo | * | * | * | * | * |

Carboxymethyl Cellulose 7M8SF, 9H, and 7H are part of the AQUALON series commercially available from Hercules.
CARBOPOL 956 is commercially available from Lubrizol.
*Data point not collected for sample.

TABLE 2B

Comparative Desensitizing Oral Care Compositions

| Ingredient | 2g Wt. % | 2h Wt. % | 2i Wt. % | 2j Wt. % |
|---|---|---|---|---|
| Carboxymethyl Cellulose | 0 | 0 | 0 | 0 |
| Glycerin USP 99.7 | 31.86 | 31.86 | 31.86 | 31.86 |
| CARBOPOL 956 | 1.0 | 4.5 | 2.0 | 1.0 |
| Xanthan Gum, NF | 5.0 | | | |
| Sodium Benzoate, NF FCC | 0.5 | 0.5 | 0.5 | 0.5 |
| Potassium Sorbate | 0.2 | 0.2 | 0.2 | 0.2 |
| Sodium Hydroxide Solution 50 | 0.25 | 2.0 | 0.75 | 0.25 |
| Potassium Oxalate Monohydrate, ACS | 3.14 | 3.14 | 3.14 | 3.14 |
| Purified Water USP | 58.05 | 57.80 | 61.55 | 63.05 |
| TEST RESULTS: | | | | |
| Complex Modulus (G*) | 1033 | 810 | 71 | 0.3 |
| Delta (Degrees) | 7.6 | 7.6 | 9.1 | 74.9 |
| Release from Release Liner (% Released) | 30 | 30 | 0 | 0 |
| $1700\ e^{(-0.05\ Delta\ Angle)}$ (Equation 1) | 1162.564 | 1162.564 | 1078.562 | 40.18057 |
| $2100\ e^{(-0.05\ Delta\ Angle)}$ (Equation 2) | 1436.109 | 1436.109 | 1332.341 | 49.63482 |
| Gel Flow off Strip | * | * | * | Yes |
| Adheres in-vivo | No | No | No | No |

Carboxymethyl Cellulose 7M8SF, 9H, and 7H are part of the AQUALON series commercially available from Hercules.
CARBOPOL 956 is commercially available from Lubrizol.
*Data point not collected for sample.

Example 2

Seven individual panelists participated in a qualitative usage study of 5 sensitivity strips. Each panelist was asked to wear 3 of the 5 strips. Panelists were instructed to apply one strip to the outside molars of one quadrant (upper or lower) of their teeth for 10 minutes while at work during business hours (between 9 am and 3 pm). To test the ease of application and fit during use, panelists applied strips to the back molars as this has been identified as the most difficult location to apply and wear the strips. Panelists were instructed to remove the strip and asked to respond to a questionnaire. Panelists recorded evaluations (shown in Table 3) for wearing, positioning, using, "stickiness", and peeling. Each panelist was asked to repeat the process with a total of nine strips. The only difference between the strips was the length of the strip.

TABLE 3

Qualitative Evaluation of Strip Length

| | 3.0 cm | 4.0 cm | 4.5 cm | 5.0 cm | 6.0 cm |
|---|---|---|---|---|---|
| Base Size | 13 | 13 | 13 | 12 | 13 |
| Ease of handling strip with fingers (Scale +4 to −4: +4 = Like most possible, 0 = Netural, −4 = Dislike most possible) | 0.753 | 0.495 | 0.240 | −0.473 | −0.851 |
| Ease of positioning on desired area (Scale +4 to −4: +4 = Like most possible, 0 = Netural, −4 = Dislike most possible) | 0.906 | 0.880 | 0.799 | −0.858 | −0.699 |
| Strip staying in place the entire time (Scale +4 to −4: +4 = Like most possible, 0 = Netural, −4 = Dislike most possible) | 0.288 | 1.628 | 1.658 | 0.350 | 0.893 |
| Ease of removing the strip (Scale +4 to −4: +4 = Like most possible, 0 = Netural, −4 = Dislike most possible) | 1.314 | 2.050 | 1.934 | 1.671 | 2.052 |
| The size of the strip while handling prior to use (JAR Scale: −2 = Too small, 0 = Just Right, +2 = Too large) | −0.627 | −0.132 | 0.268 | 0.693 | 1.090 |
| The coverage of the strip in mouth during use (JAR Scale: −2 = Too small, 0 = Just Right, +2 = Too large) | −0.742 | 0.024 | 0.411 | 0.791 | 0.965 |

Example 3

Dentinal Flow Rate Measurement

Volumetric flow rates through cross-sections of human $3^{rd}$ molar coronal dentin are measured before and after treatment using a flow cell apparatus (FIG. 6). Twenty two coronal dentin sections of human molars are obtained by cross sectional cutting with a diamond blade saw to a thickness between 0.80 and 1.00 mm. The sections resemble disks due to the circular nature of molars. The center of the disk is dentin 90 with a thin ring of enamel around the circumference (FIG. 6). The cut dentin disks are then placed in 6.0% citric acid for two minutes followed by sonication in water and subsequent rinsing to remove the smear layer created by the cutting process. The removal of the smear layer with citric acid is an effective and well known technique to produce open dentinal tubules representative of sensitive dentin found in-vivo. Samples are then immersed in at least 10 ml of commercial phosphate (pH 7) buffer for storage at neutral pH until needed.

Figure 7:
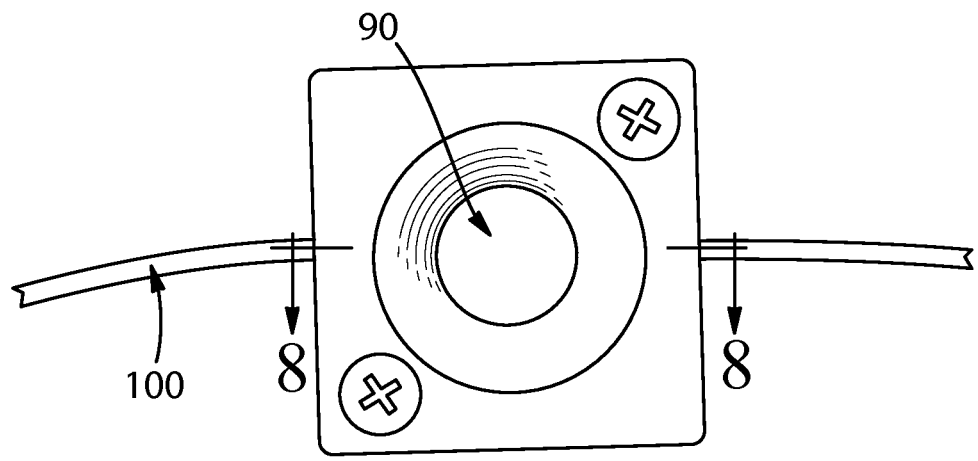
FIG. 7 is a top view of an experimental apparatus as described in Example 3.
Figure 8:
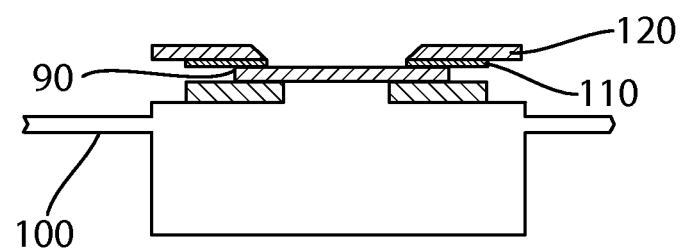
FIG. 8 is a schematic side view of an experimental apparatus as described in Example 3.

For treatment, each dentin section 90 is mounted in a Pashley-like liquid flow cell testing apparatus, as shown in FIGS. 7-8. Each dentin disk section is centered over the opening with flat washers 110 and bushing 120 on each side, making sure that the section spanned the opening with at least 1 mm overlap around the entire perimeter. Once the dentin sections are appropriately positioned, the flow cell assembly screws are tightened to hold the section in place and ensure no leakage around the rubber washers. All washers are cut with an outer diameter of ¾". The inner diameter for the bottom rubber washer is ¼" and the silicone washer on the top is ⅜". After mounting, each dentin section undergoes the following treatment sequence (1) conditioning, (2) baseline flow measurement, (3) treatment, and (4) post-treatment flow measurement.

(1) Conditioning: Hartmann's solution is applied to the dentin section at 30 psi against the non-treatment side for 45 minutes to equilibrate the dentin disk with a solution isotonic with pulpal fluid. Next, the treatment surface of each dentin section is brushed with a toothbrush for 8 minutes with Hartmann's solution while rotating the entire cell apparatus 90 degrees every 60 seconds and re-wetting the toothbrush with Hartmann's solution every 30 seconds. Each specimen is then allowed to equilibrate for 5 minutes with Hartmann's solution flowing through the section at 30 psi.

(2) Baseline Flow Measurement: A bubble is introduced into the beginning of the supply line tubing of the flow cell apparatus by releasing the pressure, loosening the fittings and raising the tubing above the flow cell test apparatus. The fittings are then retightened and 30 psi pressure is re-applied. The liquid velocity is recorded by timing the movement of the bubble within the supply line. The supply line is run across a light box and parallel to a precision ruler. Using a digital stop watch, elapsed times are recorded over 4 equidistant points along the ruler to establish the average rate the bubble travels and to ensure the velocity is constant. The linear rates are converted to volumetric flow rates by multiplying by 11.6 µl/in for 0.030" ID tubing of the supply line. Consecutive flow measurements are taken until 2 consecutive measurements vary by less than 5% to establish the baseline flow rate.

(3) Treatment: After conditioning each dentin section, the inlet fluid is switched from Hartmann's solution to an artificial pulpal fluid and allowed to flow through each section from the non-treatment side for 2 min at 30 psi. Next, the pressure is reduced to 0.43 psi and the flow cell apparatus is tipped 90°. A Kimwipe is used to absorb fluid as it drains off of the dentin surface. Note: The Kimwipe is not used to directly wipe the surface of the dentin section to avoid any surface contamination. All treatments are then applied directly to the surface of the mounted dentin disk. After treatment the section is thoroughly rinsed with Hartmann's solution. The inlet fluid source is then switched from artificial pulpal fluid back to Hartmann's solution and the flow cell is flushed by opening a dump valve downstream from the flow cell apparatus.

(4) Post Treatment Flow Measurement: For comparison to the baseline flow measurement, post treatment flow measurements are taken. Each dentin section is brushed for 2 minutes with Hartmann's solution while rotating the flow cell 45° every 10 seconds. The sections are then equilibrated with Hartmann's solution at 30 psi for 2 minutes. Flow rates are then obtained as described for the baseline flow measurements.

Volumetric flow reductions for each treated dentin disk are calculated with the following equation:

$$\% \text{ Reduction} = 100 * \frac{(Q_p - Q_b)}{Q_b}$$

Where $Q_p$=average post-treatment flow, and $Q_b$=average baseline flow.

Preparation of Hartmann's Solution (HS) (1 L)
Composition: 30 mM lactic acid, 2 mM $CaCl_2$, 5 mM KCl, 100 mM NaCl
1. Add the following to a 1 L beaker:
   3.38 g lactic acid
   0.294 $CaCl_2.2H_2O$
   0.373 g KCl
   5.844 g NaCl
2. Add approximately 600 mL of deionized water and stir until dissolved
3. Adjust the pH to 7.0 (6.5-7.5) using concentrated NaOH, then transfer to a 1 L volumetric flask
4. Fill to volume with deionized water and record final pH
5. Solution expires 6 months from making, stored at room temperature.

Preparation of Artificial Pulpal Fluid (APF) (100 mL)
1. Add 1.20 g of Bovine Serum Albumin (BSA) to a 100 mL volumetric flask.
2. Add ~50 mL of Hartmann's solution, swirl gently to solubilize albumin Make up volume (to 100%) with Hartmann's solution and invert gently to mix.
3. Solution should be stored refrigerated and used within 2 days of making.

| Reagents | Suggested Type or Source |
|---|---|
| Bovine Serum Albumin | Sigma p/n A2153-100G |
| NaCl | Sigma p/n 71379-500G |
| KCl | EMD p/n PX1405-1 |
| Lactic Acid 80% | Sigma p/n 27715 |
| $CaCl_2 \cdot H_2O$ | Sigma p/n C3881-500G |
| NaOH 50% | JT Baker p/n 3727-01 |

Example 4

Figure 9:
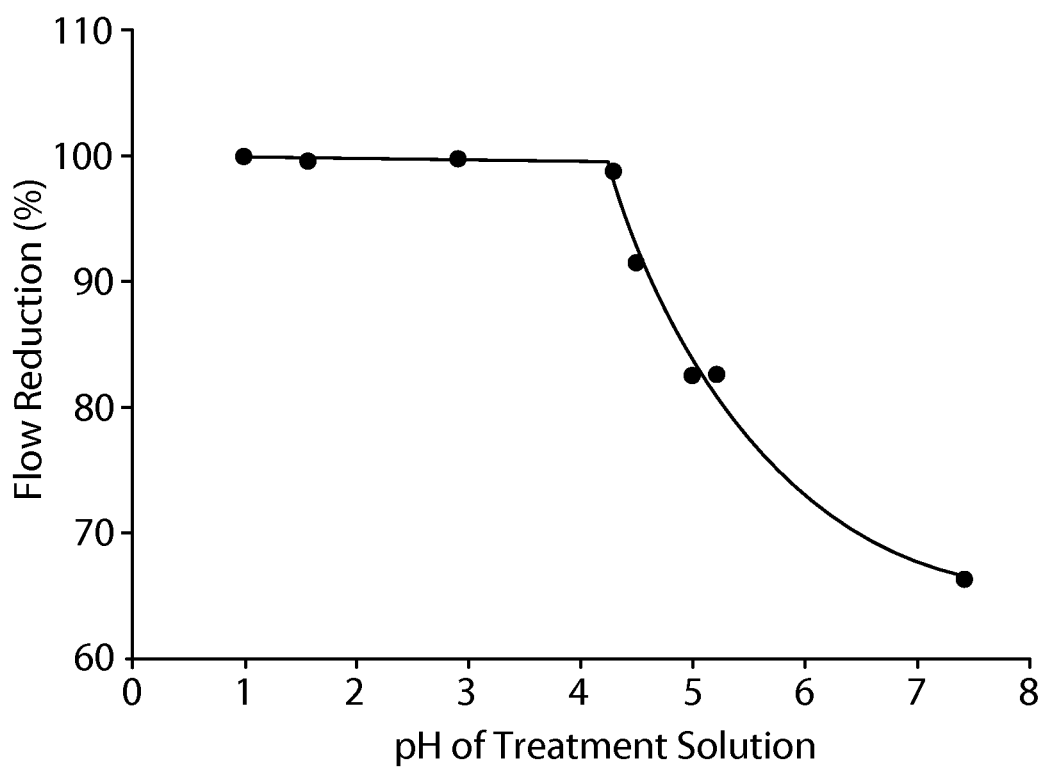
FIG. 9 is a graphical representation of Flow Reduction vs. pH, as described in Example 4.

An aqueous solution containing 3.14% potassium monohydrate and 1.5% oxalate ion (wt/wt) was tested according to the method of Example 3, except that the treatment time was extended to 10 minutes. Samples were varied by pH. A strong pH-dependence was observed, with solutions having a pH less than 4.5 essentially eliminating pulpal flow. The results are shown graphically in FIG. 9.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" The compositions herein can comprise, consist essentially of or consist of the materials set forth herein.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A desensitizing oral care composition useful for treating dentinal hypersensitivity, comprising:
   a) at least 40%, by weight of the composition, of water;
   b) from about 0.01% to about 25%, by weight of the composition, of a desensitizing agent selected from oxalic acid, salts of oxalic acid, and mixtures thereof;
   c) from about 0.1% to about 30%, by weight of the composition, of an adhesive polymer thickener;
   d) from about 0.5% to about 40%, by weight of the composition, of a secondary structuring polymer thickener;
   e) optionally from about 10% to about 40%, by weight of the composition, of a humectant; and
   f) less than 0.1%, by weight of the composition, of abrasive;
wherein the composition has a pH of less than 4.5;
wherein the composition exhibits a delta angle value of less than about 35°; and
wherein the complex modulus is according to Equation 1:

$$\text{Complex Modulus} \geq 1700 e^{(-0.05 \text{ Delta Angle})} \quad \text{(Equation 1).}$$

2. A composition according to claim 1 wherein the composition comprises at least 50%, by weight of the composition, of water.

3. A composition according to claim 1 wherein the composition comprises from about 1% to about 10% of the desensitizing agent.

4. A composition according to claim 1 wherein the composition comprises from about 0.5% to about 10% of the adhesive polymer.

5. A composition according to claim 1 wherein the composition comprises at least 30% of the humectant.

6. A composition according to claim 5 wherein the humectant comprises glycerin.

7. A composition according to claim 1 wherein the Complex Modulus is according to Equation 2:

$$\text{Complex Modulus} \geq 2100 e^{(-0.05 \text{ Delta Angle})} \quad \text{(Equation 2).}$$

8. A composition according to claim 7 wherein the composition comprises a Delta angle less than 32°.

9. A composition according to claim 8 wherein the composition comprises a Delta angle less than 30° and greater than 15°.

10. A composition according to claim 1 wherein the composition comprises the secondary structuring polymer in an amount equal to or greater than the amount of adhesive-building polymer.

11. A composition according to claim 10 wherein the ratio of the adhesive polymer to the secondary structuring polymer is from about 1:1 to about 1:5.

12. A composition according to claim 1 wherein the composition further comprises sodium hydroxide.

13. A composition according to claim 1 wherein the composition comprises from about 1% to about 6% of the desensitizing agent.

14. A composition according to claim 13 wherein the desensitizing agent is selected from potassium oxalate salts and mixtures thereof.

15. A composition according to claim 14 wherein the desensitizing agent is dipotassium oxalate.

16. A composition according to claim 15 wherein the humectant is glycerin.

17. A composition according to claim 1 wherein the adhesive-building polymer is selected from high molecular weight homo and co-polymers of acrylic acid crosslinked with a polyalkenyl polyether, and mixtures thereof.

18. A composition according to claim 17 wherein the secondary structuring polymer is selected from carboxymethylcelluloses and mixtures thereof.

19. A desensitizing oral care composition useful for treating dentinal hypersensitivity, comprising:
   a) from about 50% to about 65%, by weight of the composition, of water;
   b) from about 1% to about 5%, by weight of the composition, of a desensitizing agent selected from oxalic acid, potassium salts of oxalic acid, and mixtures thereof;
   c) from about 0.5% to about 10%, by weight of the composition, of an adhesive polymer thickener;
   d) from about 1% to about 20%, by weight of the composition, of a secondary structuring polymer thickener;
   e) from about 25% to about 40%, by weight of the composition, of a humectant; and
   g) less than 0.1%, by weight of the composition, of abrasive;
said composition having a pH less than 4.5.

20. A desensitizing oral care composition according to claim 19 wherein the composition comprises from about 1% to about 5% of the adhesive polymer thickener and from about 1% to about 10% of the secondary structuring polymer thickener.

* * * * *